United States Patent [19]

Mole

[11] Patent Number: 5,019,661

[45] Date of Patent: May 28, 1991

[54] HYDROISOMERISATION PROCESS

[75] Inventor: Thomas Mole, Surrey Hills, Australia

[73] Assignees: Commonwealth Scientific and Industrial Research Organisation; Broken Hill Proprietary Company Limited, both of Melbourne, Australia

[21] Appl. No.: 360,183

[22] Filed: Jun. 1, 1989

Related U.S. Application Data

[63] Continuation-in-part of Ser. No. 143,645, Nov. 13, 1988, abandoned.

[30] Foreign Application Priority Data

Jan. 15, 1987 [AU] Australia ............................ PH9877

[51] Int. Cl.$^5$ .............................................. C07C 5/13
[52] U.S. Cl. .................................. 585/253; 585/739; 585/751
[58] Field of Search ............... 585/253, 277, 739, 751, 585/700

[56] References Cited

U.S. PATENT DOCUMENTS

| | | | |
|---|---|---|---|
| 3,542,671 | 11/1970 | Pollitzer et al. | 208/136 |
| 3,702,886 | 11/1972 | Argauer et al. | 234/328 |
| 3,709,979 | 1/1973 | Chu et al. | 423/328 |
| 3,723,554 | 3/1973 | Wilhelm | 260/668 |
| 3,749,752 | 7/1973 | Pollitzer et al. | 260/683.9 |
| 3,796,766 | 3/1974 | Hayes et al. | 260/676 |
| 4,070,411 | 1/1978 | Butter et al. | 260/676 |
| 4,623,526 | 11/1986 | Leen | 423/277 |

OTHER PUBLICATIONS

New Developments in Zeolite Science and Technology; Murakami et al ed.; Elsevier 1986.

*Primary Examiner*—Patrick P. Garvin
*Assistant Examiner*—G. Fourson
*Attorney, Agent, or Firm*—Armstrong, Nikaido, Marmelstein, Kubovcik & Murray

[57] ABSTRACT

Branched olefins of at least 4 carbon atoms are hydroisomerized to a less branched alkane by contact with a hydrogen containing gas and a shape selective zeolite which has at least 1 metal of the Pt group supported primarily within the channels of said zeolite.

11 Claims, No Drawings

HYDROISOMERISATION PROCESS

This application is a continuation-in-part of application Ser. No. 143,645 filed Jan. 13, 1988 now abandoned. This invention relates to the hydroisomerisation of olefinic hydrocarbons to paraffinic hydrocarbons by the use of a high-silica zeolite or zeolite-like catalyst containing a metallic component of the platinum group.

It is known to those skilled in the art that:

olefinic hydrocarbons can be hydrogenated to paraffinic hydrocarbons by contact with a catalyst of the platinum group, such as platinum itself or palladium, in the presence of hydrogen.

olefinic hydrocarbons can be isomerised by contact with acid catalysts.

It is likewise known that the isomerization and hydrogenation processes can be combined as a hydroisomerization process, whereby an olefinic hydrocarbon and hydrogen are contacted together with a catalyst, with the object and effect of converting an olefinic hydrocarbon with a less branched skeleton to a paraffinic hydrocarbon with a more branched skeleton. Such hydroisomerization processes are disclosed in U.S Pat. Nos. 3,749,752 and 3,796,766 and in European Patent No. 49,803.

Hydroisomerization catalysts of the prior art have two components; first an acidic component, such as alumina or silica-alumina whether alone or with inclusion of a zeolite; and second a metal most commonly of the platinum group.

The first component serves as an acid and also as a support for the metal of the platinum group. In general, where the first component contains large amounts of alumina or silica-alumina then it may be expected that the metal of the platinum group will be supported upon the surface of the alumina or silica-alumina, rather than within the molecular channels and cavities of the zeolite. Thus, the hydrogenation step effected by the metal will be divorced from any shape-selectivity which the zeolite might impose.

Pollitzer, in U.S. Pat. No. 3,542,671 teaches the hydroisomerisation of light olefins to a product rich in branched-chain paraffins, over a hydroisomerisation catalyst having a noble metal supported by a zeolite and a larger amount of a conventional support such as silica-alumina or fluorided alumina.

Likewise, Wilhelm, in U.S. Pat. No. 3,723,554 teaches the use of platinum supported on alumina to hyroisomerise a less branched alkane to a more highly branched alkane.

Thermodynamic equilibrium between the isomeric alkanes of any carbon number at temperatures in the 150°–250° C. range of present concern favours the branched chain alkanes over the straight chain alkanes. The following table gives the theoretical composition of an equilibrium mixture of hexane isomers at 223° C. (Source: CSIRO Thermochemistry System Program Package, CSIRO, Australia).

TABLE

| Equilibrium between hexane isomers at 223° C. | |
|---|---|
| n-hexane | 14% |
| 2-methylpentane | 30% |
| 3-methylpentane | 14% |
| 2,2-dimethylbutane | 31% |
| 2,3-dimethylbutane | 11% |

Thus, the prior art on hydroisomerisation teaches exclusively how a paraffin or mixture of paraffins may be isomerised leading to a composition more nearly characteristic of thermodynamic equilibrium and how an olefin or mixture of olefins may be hydrogenated to a mixture of paraffins more nearly characteristic of thermodynamic equilibrium than the composition that would have been obtained by simple hydrogenation without skeletal rearrangement.

It is further known that shape-selective catalysts prepared by introducing a metal of Group VIII of the Periodic Table, such as platinum, palladium, ruthenium, rhodium, osmium, iridium or nickel, into a high-silica zeolite such as ZSM-5 zeolite, can be used to hydrogenate less highly substituted or branched olefins selectively in the presence of more highly substituted or branched olefins. Dessau, in J. Catalysis Vol. 77 (1982) pp. 304 and Vol 89 (1985) pp 520, teaches the selective hydrogenation of less branched olefins in the presence of more highly branched olefins over platinum/ZSM-5 catalysts at temperatures up to 275° C. He also teaches the isomerisation of olefins by migration of the double bond within the carbon skeleton of an olefin, but not by skeletal isomerisation, over the proton form of ZSM-5 zeolite at temperatures up to 200° C.; thus hexene-1 is isomerised to hexene-2.

It has hitherto been unknown that the catalyst and process conditions for hydroisomerisation can be so selected that an olefin with a more branched skeleton can be hydroisomerised to a mixture of paraffins in which paraffins of less branched skeletons are abundant. The abundance of the less branched paraffins is not limited by thermodynamic equilibrium. Thus, a branched-chain hexene may give more than 40% n-hexane at a reaction temperature of about 223° C.

BRIEF SUMMARY OF THE INVENTION

It is an object of the present invention to provide a process whereby olefinic feedstocks may be hydroisomerised to paraffinic feedstocks and specific catalysts therefor. The process is characterised by the paraffinic products having, on average, less highly branched carbon skeletons than the olefins from which they are derived.

By way of example, 2-methylpent-1-ene or 3,3-dimethylbut-1-ene may be hydroisomerised to a product containing large amounts of n-hexane.

Accordingly, the invention provides a single-stage process for the shape-selective hydroisomerization of a branched olefin of at least 4 carbon atoms to produce a less branched paraffin product, said process comprising contacting said olefin and a hydrogen-containing gas with a zeolite or zeolite-like catalyst containing at least one metal of Group VIII and in which a major portion of said at least one of these metals is supported within the molecular channels and cavities of the said catalyst, said process being conducted under conditions such that hydroisomerization predominates over both simple hydrogenation and cracking. The term "supported" means both exchanged metals and metals occluded within the cavities of the zeolite. The olefin reactant may be a gaseous or liquid hydrocarbon of 4 or more carbon atoms and in particular, one or more components of a mixture of hydrocarbons boiling in the kerosine and distillate ranges (typically 196°–317° C.). The catalyst may be ZSM-5 zeolite which may contain other metals in addition to the metals of the platinum group, e.g. boron, gallium and iron, with or without aluminium.

DETAILED DESCRIPTION OF THE INVENTION

The invention utilizes zeolites of high silica content, which have cation exchange properties and display shape-selectivity in their catalytic and sorptive properties. The term zeolite is conventionally applied to aluminosilicates, of natural or synthetic origin, in which the aluminosilicate framework is anionic and contains channels and interconnecting voids, which contain cations and water molecules, the cations being exchangeable and the water molecules being in many cases removeable without loss of the zeolite structure, so allowing the sorption of other molecules such as, for example, olefins and alkanes. However, elements other than silicon, aluminium and oxygen can be introduced into the framework of a zeolite, either at the time when the zeolite is prepared or subsequently. Accordingly, the process of the invention is not limited to the use of aluminosilicates, but includes materials of zeolite-like composition and properties containing such elements as boron, gallium, and iron, whether with or without aluminium, provided that such materials are highly siliceous and show cation-exchange and shape-selective properties like the aluminosilicate zeolites to which the process of the invention particularly applies.

In specifying zeolites and zeolite-like catalysts and compositions, we follow the usage recommended by Professor Meier in his plenary lecture "Zeolites and Zeolite-like Materials" delivered to the 7th International Zeolite Conference in Tokyo, 1986 and published in 'New Developments in Zeolite Science and Technology', editors Y. Murakami, A. Iijima and J. W. Ward, Elsevier, 1986, p. 13 et seq., which are incorporated herein by reference.

Professor Meier states (loc. cit. page 13): 'extensive isomorphous substitution of framework atoms and numerous structural analogues of aluminosilicate zeolites, as well as other recent developments in zeolite structural chemistry, make it seem logical not to impose artificial limits to this class of porous crystalline materials'.

In particular, we include within the class of zeolite-like materials to which the present invention applies those materials related to the appropriate aluminosilicate zeolites by isomorphous substitution in the anionic skeleton of the structure. Examples of the use of zeolite-like materials isomorphously related to ZSM-5 zeolite are taught in examples 26 and 27 below.

The invention may be applied to zeolites showing shape-selectivity as defined by Csicsery (loc. cit. below) which zeolites include zeolites having the skeletal structure of mordenite and offretite, and may also be applied to ferrierite, ZSM-5, ZSM-11, ZSM-12 zeolites.

The method of the invention applies particularly to highly siliceous zeolites. Highly siliceous can be defined as having an $SiO_2$ content greater than 80 wt %. Of particular interest are zeolites of the mordenite types and the pentasil zeolites, including ZSM-5 and ZSM-11. The zeolites are characterised by free aperture sizes governed by rings of 12 or 10 T atoms respectively, where T is an atom of an element such as silicon or aluminium, or such other element as boron, gallium or iron, and where the T atoms are joined together through oxygen atoms. The term "free aperture" follows the usage of D. W. Breck, *Zeolite Molecular Sieves*, Wiley, 1974.

The lower limit to free aperture size of the zeolite is set by the ability of the reactant molecule to enter the zeolite voids. Thus, the zeolite is required to admit a branched olefin which is to be isomerised and hydrogenated to a less branched paraffin.

The lower limit may be circumvented advantageously to some extent by use of zeolite having particles of particularly high surface area, which property may be distinguished by transmission electron microscopy and is not to be confused in the case of a porous material such as a zeolite with surface area measured by the simple BET method. Thus, ZSM-5 zeolite may be prepared with various morphologies depending on the method of preparation and the morphologies may be distinguished by transmission electron microscopy. Many of the morphologies are characterized by well defined crystal faces with dimensions of the order of 0.1 micron or greater. Such morphologies include picket-end laths with a longest-dimension in the range 0.1 to 5 microns, spheral aggregates of laths radiating from a centre, and bulky intergrown crystals having lengths, diameters and the thicknesses of the order of 0.5 micron or greater.

By contrast the zeolite particles of particularly high surface area, which hereinafter we refer to as "high-area" zeolite, comprise particles having overall dimension of the order of 0.1 micron. However, such a particle comprises many platelets of very much smaller dimension. The platelets are joined together, but the mass of platelets comprising the particle is penetrated by voids with dimensions comparable with those of the platelets.

Conversely, the upper limit to free aperture size will be set by the need to reduce isomerisation to more highly branched isomers. The constraint will be to allow entry of the pertinent branched olefin but not ready egress of more highly branched paraffins. Thus, the zeolite of choice may vary according to the degree of branching in the olefin feed.

The property of shape-selectivity has been described by Csicsery, in "Zeolite Chemistry and Catalysis", ACS Monograph 171 (1976) pp 680 (edited by Rabo) and by Weisz in "Proceedings of the 7th International Congress of Catalysis", Tokyo (1980) (Vol.A, p. 3). The method of the invention is applicable to zeolites displaying the property of shape-selectivity.

The process of the invention requires that one or more metals of Group VIII be incorporated into the zeolite or zeolite component. Such metals may be introduced prior to or during zeolite synthesis or subsequent to synthesis. In particular, the process of the invention requires that the metal or metals be so introduced that much of the metal content is within the channels and cavities of the zeolite structure. In a preferred method of preparing the catalyst for the process of the invention, the metal or metals are introduced into the zeolite, whether alone or compounded with silica or alumina or another oxide or clay, subsequent to the synthesis of the zeolite. Such introduction may be effected by various means, including impregnation with an aqueous or non-aqueous solution of one or more compounds of these metals.

In a preferred method of catalyst preparation where the zeolite is free of binders which strongly sorb the impregnating compound, the zeolite is impregnated by an aqueous solution of a platinum salt, such as chloroplatinic acid. In another particularly preferred method, advantage is taken of the cation exchange property of the zeolite and the zeolite undergoes cation exchange with an aqueous solution of a tetrammineplatinum salt.

All metals of Group VIII of the Periodic Table may be used but the metals of the platinum group and nickel are preferred. The platinum group comprises platinum, palladium, ruthenium, rhodium, osmium and iridium. These metals may be used singly or in combination with each other or with other metals such as zinc, iron, gallium. Of the metals of the platinum group, platinum itself is particularly preferred. The content of metals of the platinum group in the zeolite catalyst is preferably in the range of 0.05 to 5 wt %, preferably 0.1 to 3 %wt, and in the particularly preferred case where platinum alone is used, the preferred platinum content is 0.2 to 1.5 wt %.

The preparation of metal loaded zeolites is described in chapters 10 and 12 of "Zeolite Chemistry and Catalysis" ACS Monograph 171, ed. J. A. Rabo.

In the present invention, it is necessary that the metals of the platinum group introduced into the zeolite-like catalyst be reduced, and that they be so obtained and retained in such a reduced form in a high state of dispersion by methods familiar to those skilled in the art. Reduction may be achieved by treatment with hydrogen gas, either alone or admixed with inert gases or reactive gases, including the vapour of the olefinic feed utilized in the process of the invention, either in situ or prior to the practice of the process of the invention. Reduction may also be achieved by the use of a reducing agent other than hydrogen gas, such as, for example, hydrazine hydrate.

It is an important characteristic of the process of the invention that the catalyst utilized is bifunctional, combining the hydrogenation function of metals of the platinum group with acidic properties of the zeolite itself. Such acidic properties are conferred by the presence of cations of appropriate type in appropriate quantities. More specifically, the acidic properties are conferred by the presence of protons (hydrogen cations) and multivalent cations, such as, for example, $Zn^{2+}$, either singly or in combination with each other, in such amounts as to balance the negative charge of the zeolite, either totally or in part. Such protons and/or multivalent cations may be accompanied by univalent cations, such as alkali metal cations, most commonly sodium or potassium, which do not themselves effectively confer the desired acidity. A hydrogen cation may be introduced by treatment with mineral or other acid or by decomposition of the ammonium form or a tetraalkylammonium form or some other organoammonium form of the zeolite. Reduction of noble metal compounds to the metals themselves also serves to confer acidity. Thus, when the tetrammineplatinum ion is exchanged into a zeolite, subsequent decomposition and reduction yields platinum metal and protons.

The process of the invention provides for the first time the shape-selective hydroisomerisation of an olefin with a more highly branched skeleton to paraffins with less highly branched skeletons. The departure of the process from the prior art lies in the use of a zeolite or zeolite-like component capable of shape-selectivity, either alone or in combination with the metal of the platinum group, combined with the metal or metals of the platinum group as a second component, the second component being introduced in such a manner as to be largely supported within the molecular channels and cavities of the zeolite, further combined with a choice of hydroisomerisation conditions, particularly of temperature, such that the hydroisomerisation predominates over both simple hydrogenation and cracking.

The process of the invention cannot be applied to paraffins, so as to isomerise a more branched paraffin in counter-thermodynamic manner to less highly branched paraffins. It is a characteristic of the process that a temperature be selected for the process less than the temperature at which the paraffin products undergo hydroisomerisation over the catalyst applied to the process.

The process of the invention may be understood (without being bound by any theory) in the following terms. The catalyst is bifunctional. The zeolite component serves to isomerise the olefinic reactant, both by shift of the double bond and more importantly by skeletal rearrangement. The platinum group metal component serves to hydrogenate the double bond to give a paraffin. Such hydrogenation is not substantially shape-selective if the metal is supported in the conventional manner upon the external surface of a particle of a support, such as alumina. However, when the metal is supported within the molecular channels and cavities of a zeolite, the olefin and hydrogen have to combine at the surface of the metal within the confines of the zeolite, in which circumstance it may be understood that the olefins with less branched skeletons undergo hydrogenation more readily, thereby being converted to paraffins with less branched skeletons, whereas the olefins with more branched skeletons are more likely to undergo isomerisation before hydrogenation. The shape-selectivity is not imposed by the zeolite alone, but by the platinum group metal particles within the zeolite, for which reason it is important that the platinum group metals be dispersed mainly within the channels and cavities of the zeolite. For this reason, zeolites having larger pore dimensions, for example, mordenite which has channels bounded by rings of 12 T atoms, may be applied.

It is not essential that the isomerisation be confined to the channels and cavities of the zeolite. Where the reactant olefin can enter the zeolite channels freely, no advantage will obtain to isomerisation at the external surface of the zeolite particle. However, where the olefin is so highly branched as to impede free sorption into the channels, the first stages of isomerisation may need to occur at the external surface of the zeolite. Thus, advantage may obtain from the use of zeolite particles of small size and thus of high external surface area.

The olefinic feedstock utilized in the invention may be a single olefin or a mixture of olefins, whether alone or in combination with other organic materials. The distinctive feature of the olefins used is that they mainly have branched skeletons. Such skeletons may be singly branched, in which case the present invention serves to lower the amount of hydrocarbons with singly branched skeletons and to increase the amount of hydrocarbons with unbranched skeletons. If the olefin skeletons are multiply branched, the invention serves to decrease the amount of hydrocarbons having multiply branched skeletons and increase the amount of hydrocarbons having singly branched skeletons and unbranched skeletons. In particular, the feedstock may comprise higher olefins obtained by acid-catalysed oligomerisation of light olefins, such as propene. Such oligomers commonly have a highly branched structure, which is advantageous for oligomers boiling in the gasoline range (up to 196° C.), but disadvantageous in higher boiling oligomers which have thereby poor cetane index or number. By the process of this invention, such higher boiling oligomers (boiling point 196° C.) can be upgraded into more useful transport fuelstock, in that reducing the degree of branching by the process of the invention thereby improves the cetane number of hydrocarbons.

Thus, hydroisomerisation of 2-methylpentene-1 by the present invention gives a product containing n-hexane as well as 2-methylpentane and 3-methylpentane, whilst hydroisomerisation of 3,3-dimethylbutene-1 gives a product containing n-hexane, 2-methylpentane and 3-methylpentane, as well as 2,2-dimethylbutane and 2,3-dimethylbutane.

The olefin-containing feed may be supplied to the catalyst at a weight hourly space velocity (WHSV) in the range 0.1 to 100 hr$^{-1}$, preferably 0.5 to 20 hr$^{-1}$, and may be delivered either in the vapour or liquid phase and may contact the catalyst either in the liquid or vapour phase. Hydrogen is co-fed to the catalyst in a H$_2$/olefin mole ratio of preferably 0.5 to 100, more preferably 1 to 20, and most preferably 2 to 10. The partial pressure of hydrogen may be in the range 0.1 to 100 bar, preferably 0.5 to 30 bar. The hydrogen gas may be co-fed with only the olefinic feedstock or may be diluted with a non-oxidising gas such as nitrogen.

Successful practice of the invention requires that the temperature at which the feed contacts the catalyst be carefully chosen. If too low a temperature is employed, isomerisation does not occur, and hydrogenation proceeds to give a paraffin with the same carbon skeleton as the starting olefin. Thus, 2-methylpentene-1 gives 2-methylpentane. If too high a temperature is employed, skeletal isomerisation is accompanied by the extensive occurrence of cracking reactions which convert the olefin to hydrocarbons of lower molecular weight. Under some conditions, use of an over-high temperature may also result in such undesirable side-reactions as the formation of cycloalkanes and aromatics.

At a suitable chosen temperature, the value of which is dependent upon the choice of catalyst and the process conditions other than temperature, hydroisomerisation occurs with relatively little complication due to extensive occurrence of side-reactions. The chosen temperature will generally be in the range 150°-350° C., and for preferred catalysts and process conditions generally is in the narrower range of 180°-280° C.

The present invention may be more clearly understood by means of the following examples, which illustrate various aspects of the invention together with comparative material.

EXAMPLE 1

A mixture of 186 g silica sol ("Snowtex", 40 wt % SiO$_2$), 60 g tetrapropylammonium bromide and 100 g water was blended rapidly with a solution of 10 g sodium hydroxide and 2.5 g sodium aluminate in 100 g water. The resulting gel was transferred to a pressure vessel and heated in the closed vessel at 100° C. for 6 days then at 175° C. for 2 days. The crystalline slurry of ZSM-5 zeolite so formed was filtered, washed with water, dried at 100° C., calcined at 500° C. for 16 h., then treated with excess of 0.3 molar hydrochloric acid at 100° C. to give the proton form of the zeolite, having a aluminium content of 0.93 wt % and a sodium content of 0.01 wt % (balance SiO$_2$ and residual moisture). Morphologically the zeolite comprises agglomerates (200m diameter) of small platelets, which we refer to as "high-area" zeolite.

EXAMPLE 2

The proton form of ZSM-5 zeolite prepared as in example 1 (2.5 g) was admixed with 0.125 of tetrammineplatinum dichloride in 2 g water. The pH fell below 1 immediately. After 24 h, the platinum-loaded zeolite was filtered, washed with water, and dried at 110° C. The platinum content was 2.05 wt %.

EXAMPLE 3

The platinum-loaded zeolite of example 2 was pelleted, ground and sieved to 60-80 mesh size. 0.25 g of the material was then packed into a quartz tube and treated in a stream of flowing oxygen (20 cc/min) by heating first to 150° C. at a heating rate of 5° C./min. then at 150° C. for 1 h., then heating from 150° C. to 300° C. at a heating rate of 0.5° C./min, and finally heating at 300° C. for 1 h. The catalyst so treated was cooled to room temperature, purged by nitrogen, then heated to 250° C. in hydrogen at a heating rate of 5° C./min to effect reduction.

EXAMPLE 4

0.10 g of the reduced platinum-loaded catalyst of Example 3 was packed into a tubular, atmospheric pressure microreactor, and was fed with 2-methylpentene-1 liquid (0.25 cc/h.) and hydrogen gas (300 cc/hr) at temperatures of 150°, 200° and 250° C. The reaction product was analysed by on-line gas chromatography and its hydrocarbon content was found to have the composition shown in Table 1.

TABLE 1

| | Reaction temperature | | |
|---|---|---|---|
| | 150° C. | 200° C. | 250° C. |
| | | Yield (C %) | |
| Products: | | | |
| C$_1$ hydrocarbons | 0 | 0 | 0 |
| C$_3$ hydrocarbons | 0 | 1 | 2 |
| C$_4$ hydrocarbons | 0 | 2 | 2 |
| C$_5$ hydrocarbons | 0 | 2 | 2 |
| Total C$_6$ hydrocarbons | 100 | 93 | 93 |
| The C$_6$ hydrocarbons comprised: | | | |
| 2-methylpentane | 97 | 53 | 41 |
| 3-methylpentane | 3 | 17 | 15 |
| 2,2-dimethylbutane | 0 | 0 | 0 |
| 2,3-dimethylbutane | 0 | 0 | 0 |
| n-hexane | 0 | 23 | 36 |
| olefins | 0 | 0 | 0 |

EXAMPLE 5

The experiment of Example 4 was repeated but substituting 2-methylpentane for 2-methylpentene-1 as the liquid feed. The hydrocarbon products were almost exclusively unchanged 2-methylpentane at 150°, 200° and 250° C.

EXAMPLE 6

The experiment of Example 4 was repeated but using 3,3-dimethylbutene-1 (0.25 cc/h.) as the liquid feed instead of 2-methylpentene-1. The composition of the hydrocarbon products, determined by on-line and off-line gas chromatography, is shown in Table 2.

TABLE 2

| | Reaction temperature | | |
|---|---|---|---|
| | 150° C. | 200° C. | 250° C. |
| | | Yield (C %) | |
| Products: | | | |
| $C_1$ hydrocarbons | 0 | 0 | 1 |
| $C_3$ hydrocarbons | 0 | 0 | 3 |
| $C_4$ hydrocarbons | 0 | 1 | 2 |
| $C_5$ hydrocarbons | 2 | 2 | 3 |
| Total $C_6$ hydrocarbons | 98 | 96 | 91 |
| The $C_6$ hydrocarbons comprised: | | | |
| 2-methylpentane | 12 | 45 | 42 |
| 3-methylpentane | 4 | 11 | 20 |
| 2,2-dimethylbutane | 25 | 6 | 2 |
| 2,3-dimethylbutane | 53 | 7 | 1 |
| n-hexane | 3 | 27 | 26 |
| olefins | 0 | 0 | 0 |

EXAMPLE 7

2,6-dimethylheptene-3 liquid (0.25 cc/h.) and hydrogen gas (300 cc/h.) were fed to 0.10 g of the catalyst of example 3 at 200° C. The composition off the hydrocarbon product was determined by on-line gas chromatography and off-line gas chromatography/mass spectrometry. 20C % of the product consisted of cracked products, mainly $C_3$–$C_6$ alkanes. 79C % was recovered as $C_9$ alkanes, namely 5C % n-nonane, 17C % methyloctanes (mainly the 2-isomer), and 56C % doubly branched nonanes (mainly 2,6-dimethylheptane).

EXAMPLE 8

The experiment of example 7 was repeated (again at 200° C.) using as liquid feed olefinic propylene-polymer gasoline, and the following composition of the hydrocarbon products was determined as in Example 7, with attention being paid to the $C_9$ hydrocarbons, which are the most abundant constituents of the polymer gasoline. The composition is compared with the product of conventional hydrogenation of the polymer gasoline over palladium-on-charcoal catalyst at room temperature, which is shown in parentheses. 51C % of the product comprised $C_9$ hydrocarbons (59C % over Pd/C). 6C % was n-nonane (less than 1C % over Pd/C), 14% comprised methyloctanes (7C % over Pd/C), and 31C % had a doubly or triply branched skeleton (51C % over Pd/C).

EXAMPLES 9-12

The following examples show that mordenite zeolites can be used, and further show that a zeolite may be modified by treatments other than ion-exchange, and additional to introduction of the metal of the platinum group, particularly by treating with a silylating agent, which is thought to improve the stability of the metal component towards migration and sintering.

EXAMPLE 9

Sodium mordenite (Norton Zeolon 100Na) of 40-60 mesh size was heated to 400° C. in a stream of argon, then heated to 180° C. in a stream of argon saturated with trimethylchlorosilane at 0° C., then again heated in pure argon at 400° C. for 1 hour.

The mordenite so treated (1.0 g) was finely ground with platinum dichloride (0.03 g) then packed into a quartz tube and heated to 400° C. in a stream of chlorine/argon gas (1/1, v/v) at 400° C. till all sublimation of platinum compounds from the sample ceased. The sample was then cooled to 250° C. in situ and purged first by nitrogen then by hydrogen. The sample, still in situ, was finally heated to 400° C. for 16 hours in hydrogen, and was then removed from the quartz tube and pressed into a disc, which was then broken and sieved to 60-100 mesh size.

EXAMPLE 10

The sodium form of the platinum-loaded, silanized mordenite, prepared as in example 9, was converted to the hydrogen form by placing in a short glass chromatography tube and eluting with 0.3 molar aqueous hydrochloric acid until the eluate was completely free of sodium ions. The catalyst so obtained was dried in an oven at 120° C. in air.

EXAMPLE 11

The hydrogen form of platinum/silanized mordenite prepared as in example 10 (50 mg) was tested as a hydroisomerisation catalyst at 150°, 200° and 250° C. by feeding to it hydrogen gas (4 cc/min) saturated with 2-methylpentene-1 at 0° C. The compositions of the hydrocarbon products, determined by gas chromatography, are shown in Table 3.

TABLE 3

| | Temperature | | |
|---|---|---|---|
| Product distribution (C %): | 150° C. | 200° C. | 250° C. |
| C2-C5 hydrocarbons | 1 | 10 | 25 |
| 2-methylpentane | 83 | 31 | 22 |
| 3-methylpentane | 12 | 17 | 13 |
| n-hexane | 4 | 36 | 38 |

EXAMPLE 12

The experiment of example 11 was repeated using 3,3-dimethylbutene-1 instead of 2-methylpentene-1. The product obtained at a reaction temperature of 150° C. comprised: 2C % C3-C5 hydrocarbons, 25C % 2,2-dimethylbutane, 66C % 2,3-dimethylbutane +2-methylpentane, 4C % 3-methylpentane, and 10C % n-hexane.

EXAMPLE 13

This example collects together several experiments using metals of the invention other than platinum, which are used in combination with ZSM-5 zeolite. The example illustrates the usefulness of metals of Group VIII other than platinum for the process of the invention.

TABLE 4

| EXPT. NO. | METAL CONCENTRATION | FEED | FOOT-NOTES | HYDROCARBON PRODUCTS AT 200° C. | | | | HYDROCARBON PRODUCTS AT 250° C. | | | |
|---|---|---|---|---|---|---|---|---|---|---|---|
| | | | | $<C_6$ | n-Hexane | TOTAL $C_6$ | $>C_6$ | $<C_6$ | n-Hexane | TOTAL $C_6$ | $>C_6$ |
| TMH-E27 | 1.5 wt % Pd | 2-MeP = | 1 | 0.6 | 1.0 | 99.5 | — | 16.9 | 12.6 | 80.0 | 3.5 |
| | | " | 2 | 0.2 | 1.1 | 99.8 | — | 11.0 | 10.8 | 86.9 | 2.3 |
| | | " | 3 | 1.1 | 2.9 | 94.0* | 4.8 | 17.8 | 15.1 | 64.2* | 18.1 |
| TMH-E28 | 0.63 wt % Pd | 2-MeP = | 1 | 0.2 | 1.2 | 99.7 | — | 20.4 | 25.4 | 74.4 | 5.3 |
| | | " | 4 | 0.4 | 2.5 | 99.5 | — | 34.6 | 15.7 | 55.0 | 10.6 |

TABLE 4-continued

| EXPT. NO. | METAL CONCENTRATION | FEED | FOOT-NOTES | HYDROCARBON PRODUCTS AT 200° C. | | | | HYDROCARBON PRODUCTS AT 250° C. | | | |
|---|---|---|---|---|---|---|---|---|---|---|---|
| | | | | <$C_6$ | n-Hexane | TOTAL $C_6$ | >$C_6$ | <$C_6$ | n-Hexane | TOTAL $C_6$ | >$C_6$ |
| TMH-E29 | 2.09 wt % Pd | 2-MeP = | 1 | — | 0.2 | 100.0 | — | 0.1 | 2.5 | 99.8 | — |
| | | " | 5 | 15.7 | 14.8 | 72.5 | 11.8 | 57.2 | 18.4 | 31.2 | 11.8 |
| | | " | 6 | 0.2 | 0.3 | 99.7 | — | 0.9 | 4.1 | 99.0 | 0.3 |
| THM-E30 | 2.29 wt % Ru | 2-MeP = | 7 | 3.1 | 10.0 | 81.0* | 15.9 | 27.9 | 9.1 | 46.9* | 25.2 |
| | | " | 8 | 1.6 | 5.3 | 87.4* | 11.0 | — | — | — | — |
| TMH-E31 | 0.65 wt % Ir | 2-MeP = | 7 | 10.3 | 10.6 | 84.6 | 5.1 | 39.7 | 11.7 | 49.3 | 10.8 |
| | | 3,3-Me2B = | | 3.1 | 2.9 | 97.0 | 0.2 | 41.8 | 9.5 | 48.8 | 9.4 |
| | | 2-MeP = | 9 | 3.6 | 7.1 | 93.9 | 2.4 | — | — | — | — |
| TMH-E32 | 1.2 wt % Rh | 2-MeP = | 7 | 4.3 | 11.5 | 94.7 | 1.0 | 52.3 | 10.9 | 38.0 | 9.8 |
| | | 3,3-Me2B = | | 1.6 | 2.4 | 98.7 | — | 48.6 | 8.6 | 44.8 | 6.5 |
| TMH-E33 | 0.79 wt % Ni | 2-MeP = | 7 | 2.0 | 3.5 | 88.2* | 9.4 | 17.1 | 3.2 | 60.9* | 22.1 |

FOOTNOTES:
FEED 2-MeP = represents 2-methylpentene-1,3,3-Me2B = represents 3,3-dimethylbutene-1.
1 CATALYST TESTED PRIOR TO CONDITIONING
2 CATALYST CONDITIONED AT 150° C. 5 cc/min H2 OVERNIGHT BEFORE RE-TESTING
3 CATALYST CONDITIONED AT 350° C. 5 cc/min H2 OVERNIGHT BEFORE RE-TESTING
4 CATALYST CONDITIONED AT 150° C. 5 cc/min H2 2.5 DAYS BEFORE RE-TESTING
5 CATALYST RE-TESTED AFTER FURTHER OXIDATION/REDUCTION
6 FRESH CATALYST CONDITIONED (CONVENTIONAL MANNER) PRIOR TO TESTING
7 CATALYST CONDITIONED (CONVENTIONAL MANNER) PRIOR TO TESTING
8 CATALYST FURTHER REDUCED AT 400° C. 5 cc/min H2 BEFORE RE-TESTING
9 2-METHYLPENTENE-1 REPEAT AT 200° C. NO ADDITIONAL CATALYST TREATMENT BETWEEN EXPERIMENTS
*DENOTES SIGNIFICANT OLEFINS REMAINING IN PRODUCT

EXAMPLES 14–17

Teach the significance of variation in the platinum content of ZSM-5 catalyst.

EXAMPLE 14

The experiment of example 4 was repeated but using the zeolite of example 1 with a 0.58 wt % platinum content. The product at 250° C. contained: 54% n-hexane, 20% 2-methylpentane and 6% 3-methylpentane. The n-hexane yield was 15% at 200° C., and 1% at 150° C.

EXAMPLE 15

The experiment of example 6 was operated, but using the zeolite of example 1 with 0.58 wt % platinum content. The product at 250° C. contained 50% n-hexane, 26% 2-methylpentane, 8% 3-methylpentane and 6% dimethylbutanes. The n-hexane yield was 19% at 200° C. and 1% at 150° C.

EXAMPLE 16

The experiment of example 14 was repeated with catalyst having 0.18 wt % platinum. The product from 2-methylpentene-1 at 250° C. contained 12% n-hexane.

EXAMPLE 17

The experiment of example 15 was repeated with catalyst having 0.18 wt % platinum. The product from 3,3-dimethylbutene-1 at 250° C. contained 1% n-hexane.

EXAMPLE 18

The ZSM-5 zeolite of example 1 (2 g) was treated with tetrammineplatinum dichloride (0.04 g) according to the method of example 2 and subsequently treated according to the method of example 3. The sample was at 200° C. product containing 90% 2-methylpentane and 9% 3-methylpentane, and at 300° C. product containing 37% 2-methylpentane, 24% 3-methylpentane and 26% n-hexane.

EXAMPLE 23

3,3-dimethylbutene was hydroisomerised according to the method of example 6 over the catalyst of example 22 to give at 200° C. product containing 44% 2,2-dimethylbutane and 51% 2,3-dimethylbutene, and at 300° C. product containing 33% 2-methylpentane, 23% 3-methylpentane, 7% 2,2-dimethylbutane, 10% 2,3-dimethylbutane and 22% n-hexane.

EXAMPLE 24

ZSM-:11 zeolite (1 g) was treated with tetrammineplatinum dichloride (0.04 g) according to the method of example 2 and subsequently treated according to the method of example 3 to give catalyst containing 0.91 wt % platinum and 0.68 wt % aluminium. 2-Methylpentene-1 was hydroisomerised according to the method of example 4 over the catalyst so prepared. At 150° C., 99% of the product comprised 2-methylpentane. At 250° C. the product contained 40% n-hexane, 40% 2-methylpentane and 18% 3-methylpentane.

EXAMPLE 25

The catalyst of example 24 was used to hydroisomerised 3,3-dimethylbutene-1 according to the method of example 6. The product obtained at 150° C. contained 86% 2,2-dimethylbutane with 13% 2,3-dimethylpentane. The product obtained at 300° C. contained 16% n-hexane, 27% 2-methylpentane, 19% 3-methylpentane, 26% 2,2-dimethylbutane and 7% 2,3-dimethylbutane. at 200° C. product containing 90% 2-methylpentane and 9% 3-methylpentane, and at 300° C. product containing 37% 2-methylpentane, 24% 3-methylpentane and 26% n-hexane.

EXAMPLE 23

3,3-dimethylbutene was hydroisomerised according to the method of example 6 over the catalyst of example 22 to give at 200° C. product containing 44% 2,2-dimethylbutane and 51% 2,3-dimethylbutene, and at 300° C.

EXAMPLE 24

ZSM-11 zeolite (1 g) was treated with tetrammineplatinum dichloride (0.04 g) according to the method of example 2 and subsequently treated according to the method of example 3 to give catalyst containing 0.91 wt % platinum and 0.68 wt % aluminium. 2-Methylpentene-1 was hydroisomerised according to the method of example 4 over the catalyst so prepared. At 150° C., 99% of the product comprised 2-methylpentane. At 250° C. the product contained 40% n-hexane, 40% 2-methylpentane and 18% 3-methylpentane.

EXAMPLE 25

The catalyst of example 24 was used to hydroisomerised 3,3-dimethylbutene-1 according to the method of example 6. The product obtained at 150° C. contained 86% 2,2-dimethylbutane with 13% 2,3-dimethylpentane. The product obtained at 300° C. contained 16% n-hexane, 27% 2-methylpentane, 19% 3-methylpentane, 26% 2,2-dimethylbutane and 7% 2,3-dimethylbutane.

EXAMPLES 26-27

Examples 26-27 teach the use of non-aluminosilicate zeolites.

EXAMPLE 26

The experiment of example 4 was repeated using a ferrasilicate zeolite of ZSM-5 structure, activated according to the procedure of examples 2 and 3. The catalyst contained 1.23 wt % iron and 0.18 wt % platinum. 2-methylpentene-1 at 250° C. gave a product containing 26% n-hexane.

EXAMPLE 27

The experiment of example 26 was repeated using a gallosilicate of ZSM-5 structure containing 2.98 wt % gallium and 0.90 wt % platinum. 2-methylpentene-1 at 250° C. gave a product containing 42% n-hexane.

EXAMPLES 28-32

These examples teach the advantage of using "high-area" zeolite such as that in example 1 for hydroisomerisation of highly branched olefins such as dimethylbutene-1.

EXAMPLE 28

The experiment of example 14 was repeated but utilizing a catalyst prepared from ZSM-5 zeolite of spheral aggregate morphology which differs from that of example 14 in not being a "high-area" zeolite. The catalyst contained 0.96 wt % aluminium and 0.86 wt % platinum. The product at 250° C., from 2-methylpentene-1 feed, contained 56% n-hexane, 31% 2-methylpentane and 10% 3-methylpentane, with only 3C % of the product being hydrocarbons of 6 carbon atoms.

EXAMPLE 29

The experiment of example 15 was repeated with the catalyst of experiment 28. The product at 250° C. contained 25% n-hexane, 45% 2-methylpentane, 13% 3-methylpentane, 1% 2,2-dimethylbutane and 5% 3-methylbutane.

EXAMPLE 30

The catalyst of experiment 28 was used to repeat the experiment of Example 8. The propylene polymer gasoline gave at 200° C. a product of which 58% was $C_9$ hydrocarbons. The product contained in particular 1% n-nonane and 2% methyloctanes.

EXAMPLE 31

The catalyst of example 14 was used to repeat the experiment of example 8. Then propylene polymer gasoline gave at 200° C. a presence of which 54% was $C_9$ hydrocarbons. The product contained 3% n-nonane and 15% methyloctanes.

EXAMPLE 32

Two samples of ZSM-5 zeolite were prepared the one of conventional (spheral aggregate) morphology and the other being a "high-area" zeolite, as in example 1, each having a 0.44 wt % aluminium content. Each was treated according to the method of examples 2 and 3 so as to have a 0.80 wt % platinum content. Each of the catalysts was used to hydroisomerise propylene polymer gasoline according to the method of example 8. At 150° each of the catalysts gave product containing 56-62% $C_9$ hydrocarbons, including 51-58% $C_9$ hydrocarbons having two or more chain branches. At 200° the "high-area" zeolite catalyst gave product containing 5% n-nonane, 15% methyloctanes and 36% more highly branched nonanes, whereas the other catalyst gave 2% nonane, 11% methyloctanes and 42% more highly branched nonanes. At 230° C. the "high-area" zeolite catalyst gave 10% n-nonanes 14% methyloctanes and 6% more highly branched nonanes, whereas the other catalyst gave 6% n-nonanes, 8% methyloctanes and 13% more highly branched nonanes.

EXAMPLE 33

A sample of "high-area" ZSM-5 zeolite prepared according to the general procedure of example 1, but with less sodium aluminate so as to give zeolite of 0.44 wt % aluminium content, was loaded with 0.34 wt % platinum according to the procedure of example 2. 1.0 g of the catalyst was then packed into a stainless steel tubular reactor (of 10.5 mm internal diameter) and activated by treatment first in flowing oxygen (200 cc/min) then flowing hydrogen (200 cc/min) at 1 bar pressure following the procedure of example 3.

The reactor was then fed from the top with hydrogen (100 cc/min) and propylene polymer gasoline (6 cc/hr) and maintained at a pressure of 10 bar by a pressure control valve at its lower exit end. At a reactor temperature of 200° C., the product contained 10% n-nonanes, 8% methyloctanes and 44% more highly branched nonanes. At 250°, the corresponding yields were 3%, 16% and 33% respectively.

It will be clearly understood that the invention in its general aspects is not limited to the specific details referred to hereinabove.

I claim:

1. A single stage shape selective process for the hydroisomerization of a branched olefin of at least four carbon atoms to produce a less branched alkane, said process comprising contacting the olefin and a hydrogen containing gas with a catalyst consisting essentially of a shape selective zeolite and at least one metal of the platinum group primarily supported within the molecular channels and cavities of said zeolite, said zeolite being an aluminosilicate, a metallosilicate, or an aluminosilicate containing framework atoms other than silicon or aluminum, said process being conducted under conditions in which hydroisomerization predominates over both simple hydrogenation and cracking.

2. A process according to claim 1, wherein said zeolite is a metallosilicate zeolite selected from the group consisting of borosilicate, gallosilicate and ferrasilicate.

3. A process according to claim 1, wherein the zeolite is a highly siliceous aluminosilicate.

4. A process according to claim 3, wherein said aluminosilicate is ZSM-5 zeolite.

5. A process according to claim 3, wherein said aluminosilicate is ZSM-11.

6. A process according to claim 1, wherein said catalyst, contains framework substitution elements selected from the group consisting of boron, gallium and iron.

7. A process according to claim 1, wherein the amount of platinum group metals contained in the catalyst is between 0.1 and 5.0 weight percent.

8. A process according claim 7, wherein the amount of platinum group metals contained in the catalyst is between 0.2 and 3.0 weight percent.

9. A process according claim 8, wherein the amount of platinum group metals contained in the catalyst is between 0.2 and 1.5 weight percent.

10. A process according to claim 1, in which the conversion is carried out at a temperature in the range of 150° to 250° C. WHSV 0.1 to 100 $hr^{-1}$, in the presence of hydrogen at a partial pressure in the range of 0.1 to 100 bar and a $H_2$/olefin mole ratio of 0.5 to 100.

11. A single-stage process for the hydroisomerization of branched olefins having at least 4 carbon atoms to produce less branched paraffin products, said process comprising contacting said olefin and a hydrogen-containing gas with a catalyst consisting essentially of an acidic, highly siliceous aluminosilicate which is a shape-selective zeolite having supported, primarily within the molecular channels and cavities thereof, at least one reduced-form metal of the platinum group, said process being conducted under conditions such that hydroisomerization predominates over simple hydrogenation and cracking.

* * * * *